(12) United States Patent
Prasad et al.

(10) Patent No.: US 6,545,172 B1
(45) Date of Patent: Apr. 8, 2003

(54) PROCESSES FOR THE PRODUCTION OF METHYL DITHIOCARBAZINATE

(75) Inventors: Vidyanatha A. Prasad, Leawood, KS (US); Klaus Jelich, Wuppertal (DE); Dennis E. Jackman, Prairie Village, KS (US)

(73) Assignee: Bayer Corporation, Pittsburgh, PA (US)

( * ) Notice: Subject to any disclaimer, the term of this patent is extended or adjusted under 35 U.S.C. 154(b) by 0 days.

(21) Appl. No.: 10/124,850

(22) Filed: Apr. 18, 2002

(51) Int. Cl.⁷ ............................................. C07C 333/00
(52) U.S. Cl. ........................................................ 558/233
(58) Field of Search .......................................... 558/233

(56) References Cited

U.S. PATENT DOCUMENTS

| | | | |
|---|---|---|---|
| 4,696,938 A | 9/1987 | Le | 514/343 |
| 5,861,526 A | 1/1999 | Mayes | 558/233 |
| 5,877,339 A | 3/1999 | Wasleski et al. | 558/233 |
| 6,025,514 A | 2/2000 | Jackman et al. | 558/233 |

OTHER PUBLICATIONS

Ault, "Techniques and Experiments for Organic Chemistry," 4$^{th}$ Ed., pp. 52–53 (1983).*

* cited by examiner

*Primary Examiner*—Michael L. Shippen
(74) *Attorney, Agent, or Firm*—Joseph C. Gil; Richard E. L. Henderson

(57) ABSTRACT

A process for the production of methyl dithiocarbazinate includes the steps of providing a mixture comprising hydrazine, solvent, carbon disulfide and base; adding methyl bromide to the mixture; cooling the reaction mixture; and recovering methyl dithiocarbazinate. The methyl dithiocarbazinate may be recovered by filtering the reaction mixture to yield a solid methyl dithiocarbazinate retentate and a liquid filtrate; acidifying the filtrate with a mineral acid; and adding methyl isobutylketone to the acidified filterate.

26 Claims, No Drawings

PROCESSES FOR THE PRODUCTION OF METHYL DITHIOCARBAZINATE

FIELD OF THE INVENTION

The present invention relates to processes for the production of methyl dithiocarbazinate (MDTC). More particularly, in invention relates to processes for the production of methyl dithiocarbazinate which comprise the steps of providing a mixture comprising hydrazine, solvent, carbon disulfide and base; adding methyl bromide to form a reaction mixture; cooling the reaction mixture; and recovering methyl dithiocarbazinate. The present invention further relates to processes of recovering MDTC from a reaction mixture comprising the steps of filtering the reaction mixture to yield a solid MDTC retentate and a liquid filtrate; acidifying the filtrate; and adding methyl isobutylketone to the acidified filtrate.

BACKGROUND OF THE INVENTION

Methyl dithiocarbazinate may serve as a reactant or intermediate in the preparation of useful compounds. For example, Le, U.S. Pat. No. 4,696,938, discloses a process for preparing and using methyl hydrazinecarbodithioate as a reactant in the preparation of 6-aryl-pyridine thiosemicarbazones. Le teaches that methyl dithiocarbazinate is prepared by adding hydrazine hydrate to a cooled solution of potassium hydroxide in water and 2-propanol, adding precooled carbon disulfide while maintaining the internal temperature below 10° C., stirring for a further one hour and adding cooled methyl iodide.

Mayes, U.S. Pat. No. 5,861,526, discloses a process for preparing MDTC by reacting carbon disulfide and hydrazine in the presence of a non-alcoholic solvent to form hydrazinium dithiocarbazinate and methylating said hydrazinium dithiocarbazinate with methyl bromide. Mayes teaches that the reaction of carbon disulfide and hydrazine is conducted in the presence of a non-alcoholic solvent to reduce dithiocarbazinate buildup, and that the molar ratio of solvent to carbon disulfide is from about 0.4:1 to about 3:1.

Wasleski et al., U.S. Pat. No. 5,877,339, disclose a process for preparing MDTC by reacting carbon disulfide and hydrazine in an aqueous medium in an effective ratio to form a hydrazinium dithiocarbazinate, and, without isolating the hydrazinium dithiocarbazinate, methylating the hydrazinium dithiocarbazinate in the same aqueous medium with methyl bromide. Wasleski et al. teach that the aqueous medium is selected from the group consisting of water and a mixture of water and an aprotic solvent, provided that when said aqueous medium is a mixture of water and an aprotic solvent, the aprotic solvent is used in a molar ratio of from about 0.15 to 1 mole per mole of carbon disulfide.

Jackman et al., U.S. Pat. No. 6,025,514, disclose a process for preparing MDTC by reacting carbon disulfide, hydrazine and an adjunct base in an aqueous reaction medium to form a dithiocarbazinate salt, and methylating the dithiocarbazinate salt with methyl bromide. Jackman et al. teach that the base is added in such a manner that the pH of the reaction mixture is maintained between about 8 and about 14; that the mole ratio of carbon disulfide to hydrazine to base falls in the range of (1 to 1.2):(1 to 1.2):(1 to 1.2); and that the aqueous reaction medium is selected from the group consisting of water and a mixture of water and a non-alcoholic hydrocarbon solvent.

Unfortunately, many prior art processes produce MDTC in unsatisfactory yield and purity, or require the use of relatively expensive alkylating agents, such as methyl iodide. Thus, there is a need in the art for a process for producing MDTC in high yield and purity, and which preferably employs methyl bromide as an alkylating agent. Further, there is a need for a process of recovering MDTC from a reaction mixture. Preferably the MDTC recovery process renders any resulting aqueous waste non-biotoxic and suitable for normal waste disposal.

SUMMARY OF THE INVENTION

Accordingly, it is an object of the present invention to obviate problems of the prior art. It is a further object of the present invention to provide processes for the production of MDTC in high yield and/or high purity. It is yet an additional object of the invention to provide for methods for the recovery of MDTC from the reaction mixture, and processes of treating the aqueous waste formed during the production of MDTC. These and additional objects are provided by the processes of the invention.

According to one aspect of the invention there are provided processes for the production of MDTC comprising the steps of mixing hydrazine with a solvent to form a mixture; adding carbon disulfide to the mixture; adding a base to the mixture after the addition of carbon disulfide is started; adding methyl bromide to the mixture after the addition of the carbon disulfide and base is completed; keeping the resultant reaction mixture at a temperature of from about 5° C. to about 40° C. for a period of from about 30 minutes to about 2 hours; cooling the reaction mixture to a temperature of from about 0° C. to about 15° C., and maintaining the reaction mixture at that temperature range for a period of from about 15 minutes to about 2 hours; and recovering MDTC. The solvent may be selected from the group consisting of water and a mixture of water and a non-alcoholic hydrocarbon solvent.

According to another aspect of the invention there are provided methods of recovering MDTC comprising the steps of filtering the reaction mixture to yield a solid MDTC retentate and a liquid filtrate; acidifying the filtrate with a mineral acid; and adding methyl isobutylketone to the acidified filtrate.

According to one aspect of the invention there are provided processes for the production of MDTC comprising the steps of providing a mixture comprising hydrazine and solvent; adding carbon disulfide to the mixture; after the carbon disulfide addition is completed then adding base to the mixture; after the base addition is completed then adding methyl bromide to the mixture; keeping the reaction mixture at a temperature of from about 5° C. to about 40° C. for a period of from about 30 minutes to about 2 hours; cooling the reaction mixture to a temperature of from about 0° C. to about 15° C., and maintaining the reaction mixture at that temperature range for a period of from about 15 minutes to about 2 hours; and recovering methyl dithiocarbazinate from the reaction mixture.

According to another aspect of the invention there are provided processes for the production of MDTC comprising the steps providing a mixture comprising hydrazine, solvent, carbon disulfide and base; adding methyl bromide to the mixture thereby forming a reaction mixture; cooling the reaction mixture to a temperature of from about 0° C. to about 15° C., and maintaining the reaction mixture at that temperature range for a period of from about 15 minutes to about 2 hours; and recovering MDTC.

The processes of the invention of the invention are advantageous in that MDTC may be produced with high yield (from about 89% to about 91%) and/or high purity (about 95%). Additionally, the aqueous waste formed during the MDTC production can be rendered non-biotoxic.

These and additional aspects, objects and advantages of the invention are more fully described in the following detailed description.

DETAILED DESCRIPTION

The process for the preparation of MDTC using base, hydrazine, carbon disulfide and methyl bromide can be represented as set forth below:

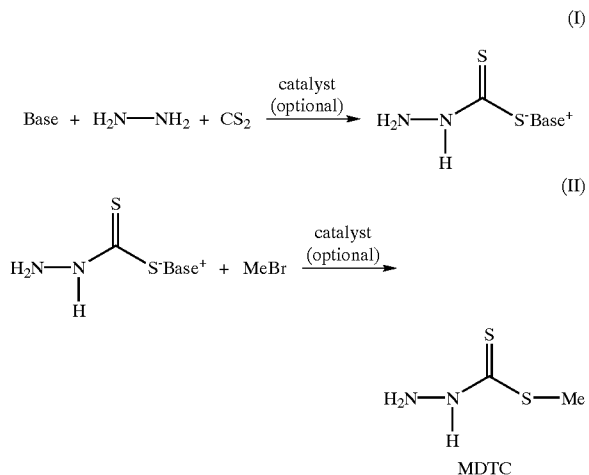

As used herein, "base" refers to a basic compound other than the hydrazine reactant. The hydrazine is preferably hydrazine hydrate.

In one embodiment of the invention, methyl dithiocarbazinate is prepared by providing a mixture comprising hydrazine, solvent, carbon disulfide and base; adding methyl bromide, thereby forming a reaction mixture, keeping the reaction mixture at a temperature of from about 5° C. to about 40° C., preferably from about 20° C. to about 30° C., for a period of from about 30 minutes to about 3 hours, preferably from about 1 to about 2 hours; cooling the reaction mixture to a temperature of from about 0° C. to about 15° C., and maintaining the reaction mixture at that temperature range for a period of from about 15 minutes to about 2 hours, preferably from about 1 to about 1.5 hours, and recovering methyl dithiocarbazinate from the reaction mixture. The MDTC may be recovered and any aqueous waste treated by filtering the reaction mixture to yield a solid MDTC retentate and a liquid filtrate; acidifying the filtrate, preferably with a mineral acid; and adding methyl isobutylketone to the acidified filtrate.

In a further embodiment, the mixture comprising hydrazine, solvent, carbon disulfide and base may be provided at a temperature of no greater than about 30° C., such as, for example, a temperature in the range of from about 5° C. to about 30° C. or in the range of from about 10° C. to about 40° C. The methyl bromide may be added over a period of time, such as from about 1 hour to about 4 hours, during which the resulting mixture is at a temperature of no greater than about 40° C., such as, for example, a temperature in the range of from about 5° C. to about 40° C.

The mixture comprising hydrazine, solvent, carbon disulfide and base may be prepared in a simultaneous add or consecutive add manner. As used herein "simultaneous add" refers to the substantially simultaneous addition of carbon disulfide and base to a mixture comprising hydrazine and solvent. As used herein "substantially simultaneous addition" is intended to mean the carbon disulfide add may have a lead time of from about 5 to about 20 minutes. The step of adding carbon disulfide and base to the mixture comprising hydrazine and solvent may be performed at a temperature of no greater than about 30° C., such as, for example, a temperature in the range of from about 10° C. to about 30° C., over a time period of from about 1 hour to about 4 hours, preferably from about 2 to about 3 hours.

In a further embodiment of the simultaneous add approach, a reactor vessel is charged with solvent and hydrazine, and carbon disulfide and base are added to a mixture of a solvent and hydrazine. The carbon disulfide add has a lead time of about 15 minutes. The carbon disulfide and base are added to the mixture at a temperature of from about 10° C. to about 30° C., preferably from about 25° C. to about 30° C., over a time period of from about 1 hour to about 4 hours, preferably from about 2 hours to about 3 hours. Following the addition of the carbon disulfide and base, methyl bromide is added to the resulting reaction mixture at a temperature of from about 5° C. to about 40° C., preferably from about 25° C. to about 30° C., over a time period of from about 1 hour to about 4 hours, preferably from about 2 hours to about 3 hours.

As used herein "consecutive add" refers to mixing hydrazine with a solvent; adding carbon disulfide to the mixture of hydrazine and solvent; and adding a base after the addition of carbon disulfide is completed. The step of adding the carbon disulfide to the mixture of hydrazine and solvent may be performed at a temperature of no greater than about 30° C., such as, for example, a temperature in the range of from about 5° C. to about 30° C., over a time period of from about 1 hour to about 4 hours, preferably from about 2 to about 3 hours. The step of adding the base may be performed at a temperature of no greater than about 30° C., such as, for example, a temperature in the range of from about 5° C. to about 30° C., over a time period of from about 1 hour to about 4 hours, preferably from about 2 to about 3 hours.

In a further embodiment of the consecutive add approach, a reactor vessel is charged with solvent and hydrazine. Carbon disulfide is then added to the mixture of solvent and hydrazine at a temperature of from about 5° C. to about 30° C. over a time period of from about 1 hour to about 4 hours. Following the addition of the carbon disulfide, a base is added to the mixture at a temperature of from about 5° C. to about 30° C. over a time period of from about 1 hour to about 4 hours. After the base has been added, methyl bromide is added to the reaction mixture at a temperature of from about 10° C. to about 40° C. over a time period of from about 1 hour to about 4 hours.

The carbon disulfide, hydrazine, base and methyl bromide are used in amounts sufficient for the desired reactions to occur. In one embodiment of the invention the carbon disulfide is present in the reaction mixture in an amount such that the molar ratio of carbon disulfide to hydrazine is from about 1.00:1 to about 1.08:1; and preferably about 1.04:1. The molar ratio of carbon disulfide to base is from about 1.04:1 to about 1.1:1; preferably about 1.08:1. The molar ratio of carbon disulfide to methyl bromide is from about 1.1:1 to about 1:1.1, preferably about 1:1.

The reaction is conducted in a pH range that does not adversely affect the reaction. Typically, the reaction may be conducted in a pH range of from about 8 to about 14, preferably from about 9 to about 14. The pH can be controlled by the rate at which the base is added. Generally the base is added slowly over a period of time.

Suitable bases for use in the processes of the present invention include inorganic bases, such as alkali metal and alkaline earth metal hydroxides, and nitrogenous bases, such as ammonia, ammonium hydroxide and amines. Suitable inorganic bases include sodium hydroxide, potassium hydroxide, lithium hydroxide and calcium hydroxide, while suitable amines include ethanolamine, di-n-propylamine, di-isopropylamine, di-n-butylamine, t-butylamine, dimethyl benzylamine, ethylmethyl pyridine, and methanediamine. In an embodiment of the invention, the base is sodium hydroxide. The sodium hydroxide may be in the form of a aqueous solution, such as 25%, by weight, aqueous sodium hydroxide.

Suitable solvents for use in the present invention include water, non-alcoholic hydrocarbon solvents, and mixtures thereof. The non-alcoholic hydrocarbon solvents include aromatic solvents such as benzene, toluene, xylene and ethyl benzene; and aliphatic solvents such as pentane, hexane, cyclohexane, and heptane. Preferred solvents include toluene. In one embodiment of the invention the solvent is a mixture of water and a non-alcoholic hydrocarbon solvent in a weight ratio of from about 1:2 to about 1:4. In one embodiment to solvent is free of alcohol.

Processes in accordance with the present invention do not require, and are preferably free of, methyl iodide. However, if desired a catalyst, such as a phase-transfer catalyst can be employed in the reaction(s). An example of the catalyst is tris-[2-(2-methylethoxy) ethyl]amine (TDA-1), N-benzyltrimethylammonium hydroxide, N-methylimidazole, dimethylamino-pyridine, 1,4-diazabicyclo-(2,2,2)-octane and diethylene glycol. The mole ratio of the catalyst can be 0 to 100 mmoles, preferably 0 to 1 mmoles, per mole of carbon disulfide.

Processes in accordance with the present invention require no isolation of intermediate dithiocarbazinate salts. Thus, in one embodiment of the invention, the reaction is conducted in a one pot process without separation or isolation of an intermediate product. However, though not required, intermediate dithiocarbazinate salts may be isolated if desired.

The MDTC may be recovered from the reaction liquor by separation methods such as, for example, centrifugation or filtration. In one embodiment the reaction mixture is filtered to yield a solid MDTC retentate and a liquid filtrate. The MDTC is allowed to air dry. The liquid filtrate, which generally comprises aqueous waste, is acidified, preferably with a mineral acid, and methyl isobutylketone is added to the acidified filtrate. Generally the methyl isobutylketone to aqueous waste volume ratio is from about 1:3 to about 1:10, preferably about 1:5. The methyl isobutylketone may then be removed, and the remaining water may be adjusted to a positive redox potential with sodium hypochlorite and then subjected to normal water disposal.

Suitable mineral acids for acidifying the liquid filtrate include hydrochloric acid, sulfuric acid and phosphoric acid, preferably the acid in sulfuric acid. Generally the aqueous waste is acidified to a pH of from about 5 to about 7, preferably to a pH of from about 5 to about 6.

The processes according to the present invention provide a MDTC yield of from about 89% to about 94%, preferably from about 91% to about 93%, and a MDTC purity of from about 93% to about 97%, preferably from about 94% to about 95%.

Throughout the examples and the present specification, parts and percentages are by weight unless otherwise specified. The following example is illustrative only and is not intended to limit the scope of the methods and fabrics of the invention as defined by the claims.

EXAMPLES

Example 1

Consecutive Add Approach

A 2000 ml reactor with mechanical stirrer and thermometer is and 291.1 grams of toluene. The mixture is agitated at 400 rpm, and 102.1 grams of hydrazine monohydrate are added over a time period of 1 minute, keeping the temperature at less than about 25° C. The mixture in the reactor is then cooled to 15° C. and 164.4 grams of carbon disulfide are added over a time period of about 2 hours. After about 5 to about 10 minutes following the carbon disulfide add, the addition of 320.0 grams of 25% aqueous sodium hydroxide is initiated. The aqueous sodium hydroxide is added over a time period of about 3 hours at a temperature of about 15° C.

Following completion of the aqueous sodium hydroxide add, 208.7 grams of methyl bromide are added to the reaction mixture over a time period of about 3 hours, while the temperature is maintained at about 30° C. The reaction mixture is maintained for one hour at 30° C. and cooled over a time period of about 30 minutes to a temperature of about 0° C. The mixture is then maintained for about 1 hour at a temperature of about 0° C.

The solids are isolated by filtration, and are then washed with cooled water and dried under vacuum. The MDTC yield is about 89.1% and the purity is about 95.2%.

Example 2

Simultaneous Add Approach

A cylindrical reactor is charged with 97.74 grams of water and 291.16 grams of toluene. The reaction mixture is agitated at 300 RPM and then cooled to a temperature of about 20° C. About 102.2 grams of hydrazine monohydrate are added to the mixture over a time period of about 15 seconds (Exotherm to a temperature of about 27° C.). The reaction mixture is cooled to a temperature of about 25° C.

Carbon disulfide (164.5 grams) and 320.0 grams of aqueous sodium hydroxide (25%) are substantially simultaneously added to the mixture, while the temperature is maintained at about 25° C. The carbon disulfide is added to the mixture dropwise over a time period of about 3 hours. About 15 minutes after the addition of the carbon disulfide is initiated, the addition of the 25% aqueous sodium hydroxide is initiated. Thus, there is an add of sodium hydroxide remaining for about 15 minutes after the carbon disulfide addition was complete.

Following completion of the carbon disulfide and sodium hydroxide add, the reaction mixture is maintained for about 1 hour at a temperature of about 25° C. The temperature is then increased to about 30° C. and the addition of 208.8 grams of methyl bromide to the mixture is initiated. The methyl bromide is added over a time period of about 3 hours. Following addition of the methyl bromide, the reaction mixture is maintained for about 1 hour at a temperature of about 30° C. The reaction mixture is then cooled to a temperature of about 5° C. and is agitated for about 1 hour.

The solid product is isolated by filtration, washed with ice water and dried on a filter for about 30 minutes. The net yield of MDTC is about 91% and the purity is about 94.2%.

Example 3

Aqueous Waste Treatment

The aqueous waste resulting from the MDTC synthesis is adjusted to a pH in the range of from about 5 to about 7, preferably from about 5 to about 6, and is extracted from about 6 to about 10 times with methyl isobutylketone. Each extraction last from about 15 to about 20 minutes, and uses a methyl isobutylketone to aqueous waste volume ratio of about 1:5. Sulfur compounds and about 98% of the residual hydrazine is removed from the acidified waste by the methyl isobutylketone extractions. The aqueous waste is then stripped of soluble methyl isobutylketone, the pH is adjusted to greater than about 10, and sodium hypochlorite solution is added until a positive redox potential, such as from about 50 to about 100 mV, is obtained.

Example 4

Aqueous Waste Treatment

The aqueous waste resulting from the MDTC synthesis is adjusted to a pH in the range of from about 5 to about 7. A 1:5 (v:v) mixture of methyl isobutylketone to aqueous waste is formed by adding methyl isobutylketone to the aqueous waste. The mixture is kept in a tank until it is slowly fed into the top of a four-stage Kunhi column as methyl isobutylketone is being pumped into the bottom of the column. The extracted aqueous waste is removed from the bottom of the column and the methyl isobutylketone is removed from the top. The bulk of the methyl isobutylketone is recovered from the organic layer by distillation. The organic residue may be disposed of by any suitable means, such as, for example, by burning. The aqueous waste pH is adjust to about 11, and the soluble methyl isobutylketone is steamed out. Sodium hypochlorite solution is then added to the aqueous waste until a positive redox potential, such as from about 50 to about 100 mV, is obtained. The aqueous waste is then suitable for normal waste disposal.

Additional embodiments and modifications within the scope of the claimed invention will be apparent to one of ordinary skill in the art. Accordingly, the scope of the present invention shall be considered in terms of the following claims, and is understood not to be limited to the details of the methods described in the specification.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of methyl dithiocarbazinate comprising:
    a) mixing hydrazine with a solvent selected from the group consisting of water and a mixture of water and a non-alcoholic hydrocarbon solvent;
    b) adding carbon disulfide to the mixture of step a) over a period of from about 1 hour to about 4 hours;
    c) from about 5 minutes to about 20 minutes after the addition of carbon disulfide is started, adding a base over a period of from about 1 hour to about 4 hours, with the temperature of the mixture being from about 5° C. to about 30° C.;
    d) after steps b) and c) are complete, adding methyl bromide over a period of from about 1 hour to about 4 hours, with the temperature of the mixture being from about 5° C. to about 40° C.;
    e) keeping the resultant reaction mixture at a temperature of from about 5° C. to about 40° C., for a period of from about 30 minutes to about 2 hours;
    f) cooling the reaction mixture to a temperature of from about 0° C. to about 15° C., and maintaining the reaction mixture at that temperature range for a period of from about 15 minutes to about 2 hours; and
    g) recovering methyl dithiocarbazinate by a process comprising
        g1) filtering the product of step f) to yield a solid methyl dithiocarbazinate retentate and a liquid filtrate;
        g2) acidifying the filtrate with a mineral acid; and
        g3) adding methyl isobutylketone to the acidified filtrate.

2. A process according to claim 1, wherein step g) further comprises:
    g4) removing the methyl isobutylketone from the acidified filtrate; and
    g5) treating the acidified filtrate with sodium hypochlorite.

3. A process according to claim 1, wherein the molar ratio of carbon disulfide to hydrazine is from about 1.00:1 to about 1.08:1.

4. A process according to claim 1, wherein the molar ratio of carbon disulfide to base is from about 1.04:1 to about 1.1:1.

5. A process according to claim 1, wherein the molar ratio of carbon disulfide to methyl bromide is from about 0.9:1 to about 1.1:1.

6. A process according to claim 1, wherein the reaction is conducted in a one pot process without separation or isolation of an intermediate product.

7. A process for the production of methyl dithiocarbazinate comprising:
    a) providing a mixture comprising hydrazine and solvent;
    b) adding carbon disulfide to the mixture at a temperature of from about 5° C. to about 30° C., over a time period of from about 1 hour to about 4 hours;
    c) after step b), adding base to the mixture at a temperature of from about 5° C. to about 30° C., over a time period of from about 1 hour to about 4 hours;
    d) after step c), adding methyl bromide to the mixture at a temperature of from about 01° C. to about 40° C., over a time period of from about 1 hour to about 4 hours, thereby forming a reaction mixture;
    e) keeping the reaction mixture at a temperature of from about 5° C. to about 40° C., for a period of from about 30 minutes to about 2 hours;
    f) cooling the reaction mixture to a temperature of from about 0° C. to about 15° C., and maintaining the reaction mixture at that temperature range for a period of from about 15 minutes to about 2 hours; and
    g) recovering methyl dithiocarbazinate from the reaction mixture.

8. A process according to claim 7, wherein step g) comprises:
    g1) filtering the product of step f) to yield a solid methyl dithiocarbazinate retentate and a liquid filtrate;
    g2) acidifying the filtrate with a mineral acid; and
    g3) adding methyl isobutylketone to the acidified filtrate.

9. A process according to claim 8, wherein step g) further comprises:
    g4) removing the methyl isobutylketone from the acidified filtrate; and
    g5) treating the acidified filtrate with sodium hypochlorite.

10. A process for the production of methyl dithiocarbazinate comprising:

a) providing a mixture comprising hydrazine, solvent, carbon disulfide and base by a process comprising
   a1) mixing hydrazine with a solvent selected from the group consisting of water, non-alcoholic hydrocarbons and mixtures thereof;
   a2) adding carbon disulfide to the mixture of hydrazine and solvent over a period of from about 1 hour to about 4 hours; and
   a3) after the addition of the carbon disulfide, adding base to the mixture of hydrazine and solvent over a period of from about 1 hour to about 4 hours;
b) adding methyl bromide to the mixture, thereby forming a reaction mixture;
c) keeping the reaction mixture at a temperature of from about 5° C. to about 40° C., for a period of from about 30 minutes to about 2 hours;
d) cooling the reaction mixture to a temperature of from about 0° C. to about 15° C., and maintaining the reaction mixture at that temperature range for a period of from about 15 minutes to about 2 hours; and
e) recovering methyl dithiocarbazinate from the reaction mixture.

11. A process according to claim 10, wherein step e) comprises:
   e1) filtering the product of step d) to yield a solid methyl dithiocarbazinate retentate and a liquid filtrate;
   e2) acidifying the filtrate with a mineral acid; and
   e3) adding methyl isobutylketone to the acidified filtrate.

12. A process according to claim 10, wherein step e) further comprises:
   e4) removing the methyl isobutylketone from the acidified filtrate; and
   e5) treating the acidified filtrate with sodium hypochlorite.

13. A process according to claim 12, wherein after the treatment with sodium hypochlorite the acidified filtrate has a positive redox potential.

14. A process according to claim 10, wherein the molar ratio of carbon disulfide to hydrazine is from about 1.00:1 to about 1.08:1.

15. A process according to claim 14, wherein the molar ratio of carbon disulfide to base is from about 1.04:1 to about 1.1:1.

16. A process according to claim 15, wherein the molar ratio of carbon disulfide to methyl bromide is from about 0.9:1 to about 1.1:1.

17. A process according to claim 10, wherein the reaction is conducted in a one pot process without separation or isolation of an intermediate product.

18. A process for the production of methyl dithiocarbazinate comprising:
   a) providing a mixture comprising hydrazine, solvent, carbon disulfide and base;
   b) adding methyl bromide to the mixture, thereby forming a reaction mixture;
   c) keeping the reaction mixture at a temperature of from about 5° C. to about 40° C., for a period of from about 30 minutes to about 2 hours;
   d) cooling the reaction mixture to a temperature of from about 0° C. to about 15° C., and maintaining the reaction mixture at that temperature range for a period of from about 15 minutes to about 2 hours; and
   e) recovering methyl dithiocarbazinate from the reaction mixture by a process comprising
      e1) filtering the product of step d) to yield a solid methyl dithiocarbazinate retentate and a liquid filtrate;
      e2) acidifying the filtrate with a mineral acid; and
      e3) adding methyl isobutylketone to the acidified filtrate.

19. A process according to claim 18, wherein step e) further comprises:
   e4) removing the methyl isobutylketone from the acidified filtrate; and
   e5) treating the acidified filtrate with sodium hypochlorite.

20. A process according to claim 19, wherein after the treatment with sodium hypochlorite the acidified filtrate has a positive redox potential.

21. A process according to claim 18, wherein the molar ratio of carbon disulfide to hydrazine is from about 1.00:1 to about 1.08:1.

22. A process according to claim 21, wherein the molar ratio of carbon disulfide to base is from about 1.04:1 to about 1.1:1.

23. A process according to claim 22, wherein the molar ratio of carbon disulfide to methyl bromide is from about 0.9:1 to about 1.1:1.

24. A process according to claim 18, wherein the reaction is conducted in a one pot process without separation or isolation of an intermediate product.

25. A process according to claim 18, wherein step a) comprises:
   a1) mixing hydrazine with a solvent selected from the group consisting of water, non-alcoholic hydrocarbons and mixtures thereof;
   a2) adding carbon disulfide to the mixture of hydrazine and solvent over a period of from about 1 hour to about 4 hours; and
   a3) after the addition of the carbon disulfide, adding base to the mixture of hydrazine and solvent over a period of from about 1 hour to about 4 hours.

26. A process according to claim 18, wherein step a) comprises:
   a1) mixing hydrazine with a solvent selected from the group consisting of water, non-alcoholic hydrocarbons and mixtures thereof;
   a2) adding carbon disulfide to the mixture of hydrazine and solvent over a period of from about 1 hour to about 4 hours; and
   a3) from about 5 minutes to about 20 minutes after the addition of carbon disulfide is started, adding a base over a period of from about 1 hour to about 4 hours.

* * * * *